United States Patent
Peterson et al.

(10) Patent No.: US 10,978,194 B2
(45) Date of Patent: Apr. 13, 2021

(54) SYSTEMS, METHODS, AND DEVICES FOR DETERMINING ENDPOINTS OF A REST PERIOD USING MOTION DATA

(71) Applicant: KONINKLIJKE PHILIPS N.V., Eindhoven (NL)

(72) Inventors: Barry Peterson, Tega Cay, SC (US); Arnaud Moreau, Vienna (AT); Peter Anderer, Vienna (AT); Marco Ross, Vienna (AT)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 437 days.

(21) Appl. No.: 15/544,144

(22) PCT Filed: Mar. 4, 2016

(86) PCT No.: PCT/IB2016/051215
§ 371 (c)(1),
(2) Date: Jul. 17, 2017

(87) PCT Pub. No.: WO2016/142815
PCT Pub. Date: Sep. 15, 2016

(65) Prior Publication Data
US 2018/0008190 A1    Jan. 11, 2018

Related U.S. Application Data

(60) Provisional application No. 62/129,226, filed on Mar. 6, 2015.

(51) Int. Cl.
*G16H 20/30* (2018.01)
*G06K 9/00* (2006.01)
(Continued)

(52) U.S. Cl.
CPC ............ *G16H 20/30* (2018.01); *A61B 5/1118* (2013.01); *A61B 5/4809* (2013.01); *G06K 9/0053* (2013.01); *G06K 9/00335* (2013.01)

(58) Field of Classification Search
None
See application file for complete search history.

(56) References Cited

U.S. PATENT DOCUMENTS

| 7,353,127 B2 * | 4/2008 | Navakatikyan ........ A61B 5/024 600/519 |
| 2010/0030118 A1 * | 2/2010 | Hiei ...................... A61B 5/1118 600/595 |

(Continued)

FOREIGN PATENT DOCUMENTS

| CN | 101287143 A | 10/2008 |
| JP | 2004097495 A | 4/2004 |

(Continued)

OTHER PUBLICATIONS

Aboy M et al., "Algorithm for Sleep/Wake Identification from Actigraphy", Proceedings of the 20th International EURASIP Conference BIOSIGNAL 2010, vol. 1, Jan. 1, 2010, p. 224-228, XP055274477, Retrieved from the Internet: URL:http://bs2010.biosignal.cz/papers/1058.pdf.

(Continued)

*Primary Examiner* — Matthew Kremer
*Assistant Examiner* — Samuel C Kim

(57) ABSTRACT

Systems, methods, and devices for determining a temporal duration of a rest period using motion data are described herein. In one exemplary embodiment, one or more data filters are applied to received motion data to generate one or more data sets of the motion data. The motion data represents an amount of activity experienced by an individual over the course of a period of time, such as one day. An iterative process is performed to identify a starting point and (Continued)

FIG. 4B an ending point of a rest period using the generated data set(s). After the starting and ending points are identified, a temporal difference between the starting and ending points is calculated, and a total temporal duration of the rest period is determined.

13 Claims, 12 Drawing Sheets

(51) Int. Cl.
*A61B 5/00* (2006.01)
*A61B 5/11* (2006.01)

(56) References Cited

U.S. PATENT DOCUMENTS

| | | | |
|---|---|---|---|
| 2012/0083705 A1* | 4/2012 | Yuen | A61B 5/0002 600/508 |
| 2012/0108999 A1* | 5/2012 | Leininger | A61B 5/0004 600/546 |
| 2013/0012836 A1 | 1/2013 | Crespo | |
| 2014/0088373 A1* | 3/2014 | Phillips | A61B 5/113 600/301 |
| 2014/0297600 A1 | 10/2014 | Kan | |
| 2015/0241407 A1* | 8/2015 | Ou | A61B 5/14532 702/19 |
| 2016/0098081 A1* | 4/2016 | Takahashi | A61B 5/681 340/5.51 |

FOREIGN PATENT DOCUMENTS

| | | |
|---|---|---|
| JP | 2006181263 A | 7/2006 |
| JP | 2011115188 A | 6/2011 |

OTHER PUBLICATIONS

Lichstein KL, Stone KC, Donaldson J, Nau SD, Soeffing JP, Murray D, Lester KW, Aguillard RN. Actigraphy validation in insomnia. Sleep 2006; 29: 232-239.

Meltzer LJ, Montgomery-Downs HE, Insana SP, Walsh CM. Use of actigraphy for assessment in pediatric sleep research. Sleep Med Rev 2012, 16: 463-475.

Malow BA, Goldman SE, Fawkes DB, Goodpaster RL, Adkins KW, Peterson BT. A novel method fo analysing actigraphy data to help identify sleep disturbance in children with autism spectrum disorder (ASD). Poster presentation at 2014 Am. Soc. Exp. Neurotherapeutics (ASENT).

Malow BA, Goldman SE, Fawkes DB, Goodpaster RL, Adkins KW, Peterson BT. A novel actigraphy analysis method or detecting the effects of treatment on disturbed sleep in children with autism. Poster presentation at 2014 Assoc. Prof. Sleep Soc (APSS) 2014.

Peterson BT, Chiao P, Pickering E, Freeman J, Zammit GK, Ding Y, Badura LL. Comparison of actigraphy and polysomnography to assess effecs of zplpidem in a clinical research unit. Sleep Med. 2013; 13: 419-424.

Denise P, Bocca ML. Effects of zolpidem 10 mg, zopiclone 7.5 mg and flunitrazepam 1 mg on night-time motor activity. Europ. Neuropsychopharmacology 2003; 13: 111-115.

Ding J, Symanzik J, Sharif A, Wang J, Duntley S, Shannon WD. Powerful actigraphy data through functional representation. Chance; 2011; 254: 30-36.

* cited by examiner

SYSTEMS, METHODS, AND DEVICES FOR DETERMINING ENDPOINTS OF A REST PERIOD USING MOTION DATA

CROSS-REFERENCE TO PRIOR APPLICATIONS

This application is the U.S. National Phase application under 35 U.S.C. § 371 of International Application Serial No. PCT/IB132016/051215, filed on 4 Mar. 2016, which claims the benefit of U.S. Application Ser. No. 62/129,226, filed on 6 Mar. 2015. These applications are hereby incorporated by reference herein.

CROSS-REFERENCE TO RELATED APPLICATION

The present application claims the benefit of U.S. Provisional Patent Application No. 62/129,226, which was filed on Mar. 6, 2015, the disclosure of which is incorporated herein by reference in its entirety.

BACKGROUND OF THE INVENTION

1. Field of the Invention

The present invention generally relates to systems, methods, and devices for determining a temporal duration of a rest period using motion data. In particular, improved techniques for determining a start time and an end time of a rest period are described herein.

2. Description of the Related Art

Actigraphy is the use of motion sensors, such as accelerometers, to record motion of an individual wearing, or having attached thereto, such motion sensors. Actigraphy enables the physical activity of an individual to be determined, measured, and assessed. There are many motion tracking devices that are commercially available that monitor, and/or analyze, an amount of activity of an individual. One particular use for such activity data is, for instance, identification of when an individual is asleep and/or awake. Periods of time when an individual is likely to be asleep are otherwise referred to as "rest periods," while periods of time when an individual is likely to be awake are otherwise referred to as "active periods."

Typically, to determine a temporal duration of a rest period, there has to be a "threshold" activity value separating active (e.g., high activity) from rest (e.g., low activity). The computational challenge is to identify a proper threshold value and to use that threshold value to identify a beginning and an end of the rest period.

One of the limitations of conventional analysis to determine endpoints for sleep is that identification of sleep/wake status on the basis of motion in comparison to an activity threshold. This can create a "threshold problem" when attempting to identify an appropriate threshold activity level to use. Attempts to maximize the agreement between actigraphy estimates of polysomnography ("PSG") endpoints to true PSG endpoints by selecting an optimal threshold activity level from discriminating between awake and sleep times. Unfortunately, these efforts have been unsuccessful, potentially because it is difficult for a single threshold activity level to accommodate for situations where a subject appears as if they are asleep, when in fact they are awake but remaining motionless.

Furthermore, stand analysis often includes manual over-reading of results, sometimes with the help of sleep diaries (which may include mistakes), or ambient light data, to minimize these errors. This process is tedious and time consuming, varies among device manufactures, and can produce values that are still estimates of endpoints that are more accurately assessed with PSG. Further still, this analysis may be missing important information in the actigraphy data.

Thus, it would be beneficial for there to be systems, methods, and devices that accurately and objectively identifies, within motion data, end points for rest periods, while also being capable of robustly performing such an analysis on large amount of motion data.

SUMMARY OF THE INVENTION

Accordingly, it is an objective of this invention to provide systems, methods, and devices that accurately and objectively identify, with motion data, beginning and end times for rest periods, while also being capable of robustly performing such an analysis on large amount of motion data.

In one exemplary embodiment, a threshold activity level is set, motion data is received, a first filter is applied to the motion data, and a first data set of the motion data is generated. A minimum point within the first data set is determined, and a minimum time associated with the minimum point is determined. A first upper intersection point where the first data set intersects with the threshold activity level, the first upper intersection point occurring after the minimum time, is determined along with a first upper time associated with the first upper intersection point. Then, a first position on the motion data corresponding to the first upper time is determined, and a raw data upper intersection point where the motion data intersects with the threshold activity level is determined. A raw data upper time associated with the raw data upper intersection point is determined, where the raw data upper time occurs after the first upper time within the rest period, and the raw data upper time is set as an upper boundary of the rest period. A first lower intersection point where the first data set intersects with the threshold activity level is determined, the first lower intersection point occurring prior to the minimum time, and a first lower time associated with the first lower intersection point is also determined. Then, a second position on the motion data corresponding to the first lower time is determined, and a raw data lower bound where the motion data intersects with the threshold activity level is also determined. A raw data lower time associated with the raw data lower bound is determined, and the raw data lower time is set as the lower boundary of the rest period. An amount of time of the rest period is then determined by calculating a temporal difference between the raw data upper time and the raw data lower time.

In another exemplary embodiment, a system is provided that includes a wearable motion tracking including at least one motion sensor. The system also includes a motion analysis device including communications circuitry that receives motion data from the wearable motion tracker, memory that stores the motion data, and at least one processor. The at least one processor is configured to set a threshold activity level for a rest period, apply a first filter to the motion data, and generate a first data set of the motion data. The at least one processor is further configured to determine a minimum point within the first data set, and a minimum time associated with the minimum point. The at least one processor is still further configured to determine a first upper intersection point where the first data set intersects with the threshold activity level, the first upper intersection point occurring after the minimum time. The at least one processor is further configured to determine a first upper time associated with the first upper intersection point, a first position on the motion data corresponding to the first upper time, a raw data upper intersection point where the motion data intersects with the threshold activity level, and a raw data upper time associated with the raw data upper intersection point, where the raw data upper time occurs after the first upper time within the rest period. The at least one processor is then configured to assign the raw data upper time as being an upper boundary of the rest period. The at least one processor is also configured to determine a first lower intersection point where the first data set intersects with the threshold activity level, the first lower intersection point occurring prior to the minimum time, a first lower time associated with the first lower intersection point, a second position on the motion data corresponding to the first lower time, a raw data lower bound where the motion data intersects with the threshold activity level, and a raw data lower time associated with the raw data lower bound. The at least one processor is further configured to assign the raw data lower time as being a lower boundary of the rest period, and to determine an amount of time of the rest period is then determined by calculating a temporal difference between the raw data upper time and the raw data lower time.

In yet another exemplary embodiment, a wearable motion tracker is provided. The wearable motion tracker includes at least one motion sensor that captures motion data representative of an amount of activity detected during each epoch within a time period, memory that stores the motion data, and at least one processor. The at least one processor is configured to set a threshold activity level for a rest period, apply a first filter to the motion data, and generate a first data set of the motion data. The at least one processor is further configured to determine a minimum point within the first data set, and a minimum time associated with the minimum point. The at least one processor, then, is configured to determine a first upper intersection point where the first data set intersects with the threshold activity level, where the first upper intersection point occurs after the minimum time, a first upper time associated with the first upper intersection point, a first position on the motion data corresponding to the first upper time, a raw data upper intersection point where the motion data intersects with the threshold activity level, and a raw data upper time associated with the raw data upper intersection point, where the raw data upper time occurs after the first upper time within the rest period. The at least one processor is also configured to assign the raw data upper time as being an upper boundary of the rest period. Then, the at least one processor is configured to determine a first lower intersection point where the first data set intersects with the threshold activity level, where the first lower intersection point occurs prior to the minimum time, a first lower time associated with the first lower intersection point, a second position on the motion data corresponding to the first lower time, a raw data lower bound where the motion data intersects with the threshold activity level, and a raw data lower time associated with the raw data lower bound. The at least one processor is further configured to assign the raw data lower time as being a lower boundary of the rest period, and to determine an amount of time of the rest period by calculating a temporal difference between the raw data upper time and the raw data lower time.

BRIEF DESCRIPTION OF THE DRAWINGS

The above and other features of the present invention, its nature and various advantages will be more apparent upon consideration of the following detailed description, taken in conjunction with the accompanying drawings in which.

DETAILED DESCRIPTION OF EXEMPLARY EMBODIMENTS

Figure 1:
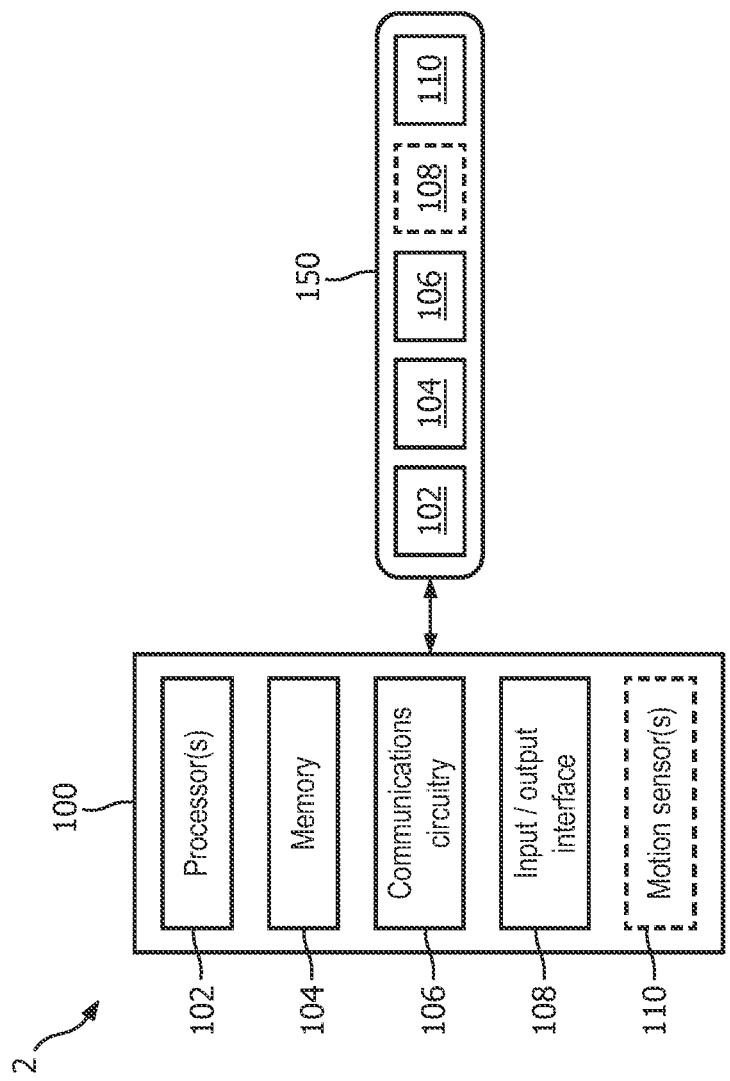
FIG. 1 is a schematic illustration of a system including a wearable motion tracker and a motion analysis device, in accordance with various embodiments.

The present invention may take form in various components and arrangements of components, and in various techniques, methods, or procedures and arrangements of steps. The referenced drawings are only for the purpose of illustrated embodiments, and are not to be construed as limiting the present invention. Various inventive features are described below that can each be used independently of one another or in combination with other features. Furthermore, as used herein, the singular form of "a", "an", and "the" include plural references unless the context clearly dictates otherwise. As employed herein, the term "number" shall mean one or an integer greater than one (e.g., a plurality). Direction phrases used herein including, but not limited to, top, bottom, right, left, upper, lower, front, back, rear, and derivatives thereof, relate to the orientation of the elements shown in the drawings and are not limiting upon the claims unless expressly recited therein.

FIG. 1 is a schematic illustration of a system 2 including a wearable motion tracker 150 and a motion analysis device 100, in accordance with various embodiments. Motion analysis device 100, for example, may correspond to any suitable type of electronic device, such as, and without limitation, a desktop computer, a mobile computer (e.g., a laptop, an ultrabook), a mobile phone, a smart phone, a tablet, a television, a set top box, a smart television, a display screen, a personal digital assistant ("PDA"), smart furniture, a smart household device, a smart vehicle, and/or a smart transportation device. In one embodiment, motion analysis device 100 includes one or more processors 102, memory 104, communications circuitry 106, and an input/output interface 108. Furthermore, in an exemplary embodiment, motion analysis device 100 also includes one or more motion sensors 110, however this is optional. Motion analysis device 100 is also structured such that one or more additional components may be included, or one or more of processor(s) 102, memory 104, communications circuitry 106, input/output interface 108, and motion sensor(s) 110 may be omitted. For example, motion analysis device 100 may include a power supply or a bus connector. In one exemplary embodiment, multiple instances of any of processor(s) 102, memory 104, communications circuitry 106, input/output interface 108, and motion sensor(s) 110 are included within motion analysis device 100, however, for simplicity, only one of each component is shown within system 2 of FIG. 1.

Processor(s) 102, in one exemplary embodiment, includes any suitable processing circuitry capable of controlling operations and functionality of motion analysis device 100, as well as facilitating communications between various components therein. Processor(s) 102, as an illustrative example, may include central processing units ("CPUs"), graphic processing units ("GPUs"), microprocessors, digital signal processors, or any other type of processor, or any combination thereof. The functionality of processor(s) 102, for instance, may be performed using one or more hardware logic components including, but not limited to, field-programmable gate arrays ("FPGAs"), application specific integrated circuits ("ASICs"), application-specific standard products ("ASSPs"), system-on-chip systems ("SOCs"), and/or complex programmable logic devices ("CPLDs"). In one embodiment, processor(s) 102 includes its own local memory, which stores program modules, program data, and/or one or more operating systems ("OSs"), however processor(s) 102 is capable of operating one or more firmware applications, media applications, and/or resident applications.

Memory 104, in the illustrative embodiment, includes one or more types of storage mediums, such as any volatile or non-volatile memory, or any removable or non-removable memory implemented in any suitable manner to store data. For example, information may be stored using computer-readable instructions, data structures, and/or program modules. Various types of memory include, but are not limited to, hard drives, solid state drives, flash memory, permanent memory (e.g., ROM), electronically erasable programmable read-only memory ("EEPROM"), CD-ROM, digital versatile disk ("DVD") or other optical storage medium, magnetic cassettes, magnetic tape, magnetic disk storage, or any other magnetic storage device, RAID storage systems, or any other type of storage, or any combination thereof. Furthermore, memory 104, in one embodiment, is implemented as computer-readable storage media ("CRSM"), which corresponds to any suitable physical media accessible by processor(s) 102 to execute one or more instructions stored within memory 104.

Communications circuitry 106, in one exemplary embodiment, corresponds to any circuitry that allows or enables motion analysis device 100 to communicate with one or more additional devices, servers, and/or systems. For example, communications circuitry 106 may facilitate communications between wearable motion tracker 150 and motion analysis device 100 via a network, such as the Internet, or using any number of suitable communications protocols. Various types of communications protocols include, but are not limited to, Transfer Control Protocol and Internet Protocol ("TCP/IP") (e.g., any of the protocols used in each of the TCP/IP layers), Hypertext Transfer Protocol ("HTTP"), and wireless application protocol ("WAP"), Wi-Fi (e.g., 802.11 protocol), Bluetooth®, radio frequency systems (e.g., 900 MHz, 1.4 GHz, and 5.6 GHz communication systems), cellular networks (e.g., GSM, AMPS, GPRS, CDMA, EV-DO, EDGE, 3GSM, DECT, IS-136/TDMA, iDen, LTE or any other suitable cellular network protocol), infrared, BitTorrent, FTP, RTP, RTSP, SSH, and/or VOIP. In one embodiment, motion analysis device 100 also includes an antenna to facilitate wireless communications with a network. In another embodiment, motion analysis device 100 includes one or more universal serial bus ("USB") ports, one or more Ethernet or broadband ports, or any other type of hardware access port so that communications circuitry 106 enables motion analysis device 100 to communicate across one or more communications networks.

I/O interface 108, in an exemplary embodiment, corresponds to any suitable mechanism for receiving inputs from a user of motion analysis device 100. For example, a camera, keyboard, mouse, joystick, or external controller may be used as an input mechanism for I/O interface 108. The output portion I/O interface 108, in one embodiment, corresponds to any suitable mechanism for generating outputs from motion analysis device 100. For example, one or more displays, may be used as an output mechanism for I/O interface 108. As another example, one or more lights, light emitting diodes ("LEDs"), and/or one or more vibrating mechanisms or other haptic features operable to provide a haptic response may be used as an output mechanism for I/O interface 108. In one non-limiting embodiment, I/O interface 108 includes a display screen and/or touch screen, which is configurable to be any size or shape, and is capable of being located at any portion on motion analysis device 100. Various types of displays may include, but are not limited to, liquid crystal displays ("LCD"), monochrome displays, color graphics adapter ("CGA") displays, enhanced graphics adapter ("EGA") displays, variable graphics array ("VGA") display, or any other type of display, or any combination thereof. Still further, a touch screen, in one embodiment, corresponds to a display screen including capacitive sensing panels capable of recognizing touch inputs thereon.

Motion sensor(s) 110 of motion analysis device 100, in one embodiment, correspond to any suitable component capable of measuring changes in motion of motion analysis device 100. For example, a motion sensor may determine a change in orientation of motion analysis device 100 with respect to gravity. Motion sensor(s) 110, in one exemplary embodiment, correspond to accelerometers, which are configured to measure an amount of acceleration along one or more axis (e.g., three-dimensional motion sensing devices). Various other types of motion sensors include, but are not limited to, cameras, capacitive sensors, Hall Effect sensors, inertial measurement units ("IMUs"), single or multi-axis gyro sensors, magnetometer sensors, or any other suitable type of motion sensor, or any combination thereof. In one embodiment, motion analysis device 100 does not, itself, include motion sensor(s) 110, and alternatively receives motion data from wearable motion tracker 150, as described in greater detail below.

Wearable motion tracker 150, in one illustrative, non-limiting embodiment, corresponds to any suitable type of wearable electronic device or portable electronic device including, but not limited to, a mobile computer (e.g., a laptop, an ultrabook), a mobile phone, a smart phone, a tablet, a watch, a bracelet, a wristband, a personal digital assistant, or any other suitable smart accessory. For example, wearable motion tracker 150 may be worn by an individual so as to capture information corresponding to an amount of activity of the individual. In one embodiment, wearable motion tracker 150 is worn on an individual's wrist, arm, leg, or chest.

In one embodiment, wearable motion tracker 150 includes one or more of processors 102, memory 104, communications circuitry 106, and one or more motion sensors 110. Furthermore, in an exemplary embodiment, wearable motion tracker 150 also includes I/O interface 108, however this is optional. In the illustrative embodiment, each of processor(s) 102, memory 104, communications circuitry 106, I/O interface 108, and motion sensor(s) 110 are substantially similar to processor(s) 102, memory 104, communications circuitry 106, I/O interface 108, and motion sensor(s) 110 of motion analysis device 100, respectively, and the previous description applies. Furthermore, each of the previous descriptions is relatable to use with wearable motion tracker 150 instead of motion analysis device 100.

Wearable motion tracker 150 may be worn by an individual throughout a period of time, such as a day (e.g., 24-hours), week, or month, for example, to record an amount of activity that the individual experiences during that period of time. After this period of time has ended, the individual provides motion analysis device 100 with the motion data obtained by wearable motion sensor 150. For example, wearable motion tracker 150 may communicate motion data captured thereon to motion analysis device 100 via a Bluetooth connection or via a hardwire connection. Motion analysis device 100 is, therefore, structured to process and analyze the motion data of the individual. For example, active periods and rest periods of the individual may be determined from the motion data by motion analysis device 100. In one exemplary embodiment, however, wearable motion tracker 150 is structured to, alternatively, analyze the motion data itself, and therefore the motion data need not be provided to motion analysis device 100. Similarly, motion data may be obtained from motion sensor(s) 110 located on motion analysis device 100, and therefore the motion data need not be received from wearable motion tracker 150. However, persons of ordinary skill in the art will recognize that either of wearable motion tracker 150 and motion analysis device 100 may obtain, process, and/or analyze motion data, and the aforementioned are merely exemplary.

Figure 2:
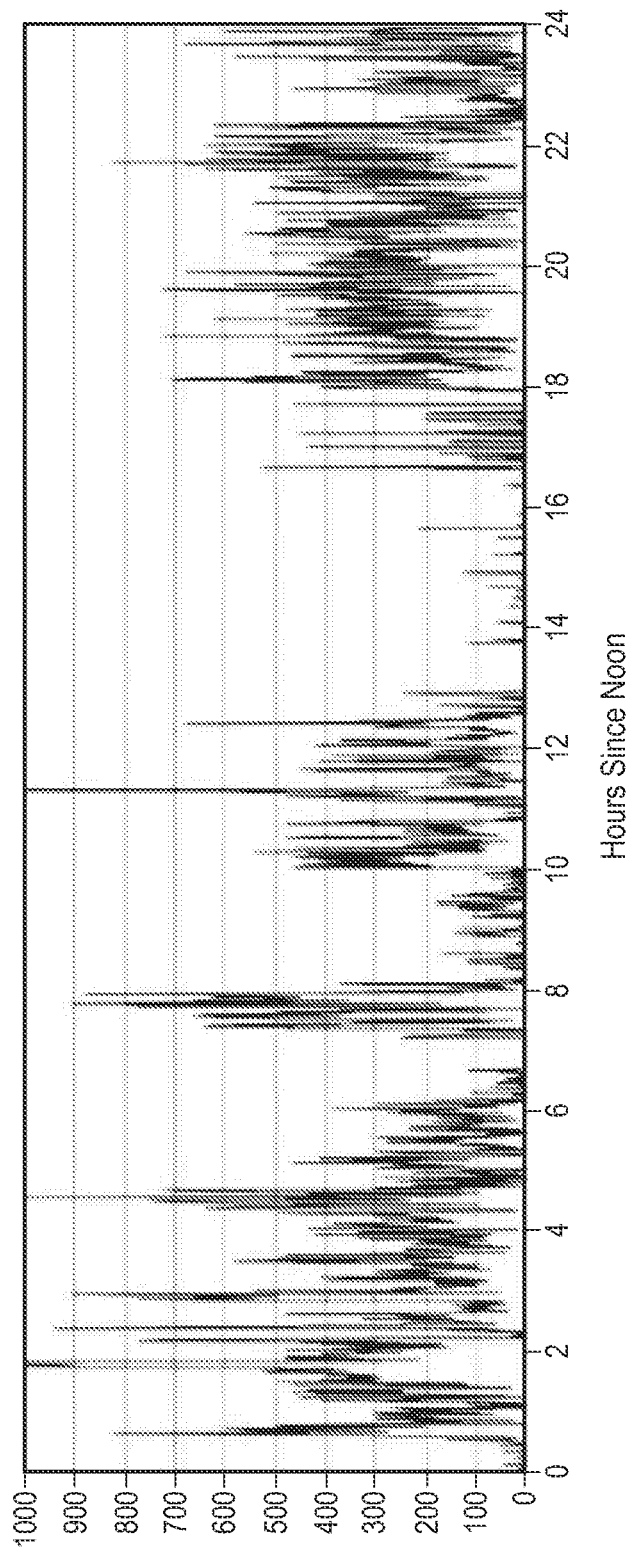
FIG. 2 is an illustrative graph of exemplary motion data obtained from a wearable motion tracker, in accordance with various embodiments.

FIG. 2 is an illustrative graph 200 of exemplary motion data obtained from a wearable motion tracker, in accordance with various embodiments. In one embodiment, graph 200 presents an amount of activity of an individual that wore a motion sensor, such as wearable motion tracker 150, recorded over a 24-hour time period. In graph 200, the x-axis is presented in terms of hours since noon (e.g., 12:00 PM). For example, at an origin of the x-axis of graph 200, a time "0" would correspond to 12:00 PM. Each subsequent demarcation on the x-axis of graph 200, therefore, corresponds to a time occurring after 12:00 PM. For example, a time "6" would correspond to 6 hours after 12:00 PM, 6:00 PM (or 18:00), whereas a time "12" would correspond to 12 hours after 12:00 PM, 12:00 AM (or 24:00) (e.g., midnight). Persons of ordinary skill in the art will recognize that any suitable time interval, and any suitable period of time may be used for graph 200, and the use of one, 24-hour period of time beginning at 12:00 PM is merely exemplary.

A y-axis of graph 200, in one embodiment, is presented in terms of an amount of activity that occurred at a particular time, in units of counts per minute. In this way, each point on graph 200 is representative of an amount of activity that an individual experienced at that particular time. As an illustrative example, at a time "8," an amount of activity that is recorded is approximately 900 counts/minute.

The unit "counts per minute," "counts/minute, or "cts/min," correspond to a measured amount of activity recorded by motion sensor(s) 110. Motion sensor(s) 110, in one embodiment, is structured to record an activity reading during each epoch (e.g., typically one minute, however any suitable temporal duration may be used). An acceleration of an individual constantly changes in all directions, and motion sensor(s) 110 is structured to sample an amount of motion (e.g., an acceleration or change in acceleration) multiple times per second. For example, motion sensor(s) 110 may have a sample rate of approximately 32 times per second. The sampled acceleration data is then collected for an epoch and combined to obtain an activity count during that epoch. Therefore, each data point within graph 200 corresponds to an aggregate amount of activity occurring during each minute over the course of a 24-hour time interval. However, persons of ordinary skill in the art will recognize that any time interval, and any suitable technique for obtaining activity data of an individual, may be employed, and the aforementioned is merely exemplary.

Figure 3:
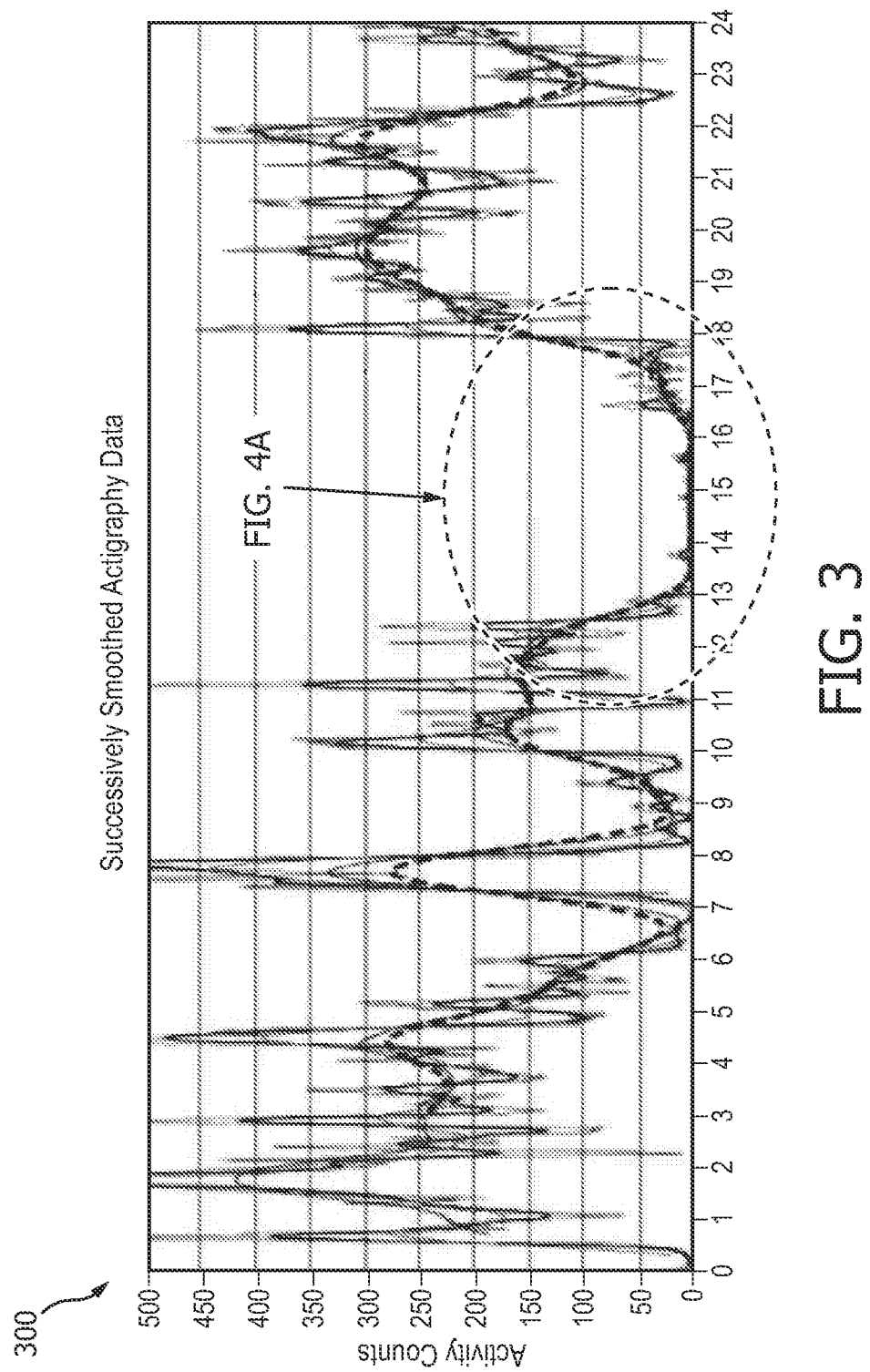
FIG. 3 is an illustrative graph of exemplary model data representative of the motion data of FIG. 2, in accordance with various embodiments.

FIG. 3 is an illustrative graph 300 of exemplary model data representative of the motion data of FIG. 2, in accordance with various embodiments. Graph 300, in the illustrative, non-limiting embodiment, includes processing the motion data five times with resultant curves, representing the five data sets, plotted along similar axes. As mentioned previously, the motion data presented within graph 200 corresponds to an amount of activity in counts per minute over a 24 hours period of time. To produce graph 300, various data processing techniques are applied to the motion data of graph 200 to generate different data sets representative of the motion data.

In one embodiment, the motion data of graph 200 is smoothed by application of a moving Gaussian window of a predetermined length to the motion data. The predetermined length of the moving Gaussian window may correspond to any suitable length between a few minutes (e.g., 5-10 minutes), and a few hours (e.g., 60-360 minutes). For example, five moving Gaussian windows having lengths of 20 minutes, 40 minutes, 60 minutes, 80 minutes, and 100 minutes may be applied to the motion data of graph 200 to generate five data sets presented within graph 300.

As an illustrative example, a moving Gaussian window of length 100 minutes is applied to the motion data of graph 200 to generate a first data set represented by curve S5; a moving Gaussian window of length 80 minutes is applied to the motion data of graph 200 to generate a second data set represented by curve S4; a moving Gaussian window of length 60 minutes is applied to the motion data of graph 200 to generate a third data set represented by curve S3; a moving Gaussian window of length 20 minutes is applied to the motion data of graph 200 to generate a fourth data set represented by curve S2; and a moving Gaussian window of length 20 minutes is applied to the motion data of graph 200 to generate a fifth data set represented by curve S1. The application of five different moving Gaussian windows to the motion data to generate five different data sets is merely exemplary, and furthermore the use of a moving Gaussian window is also exemplary, as any suitable data filter may alternatively be used.

Figure 4A:
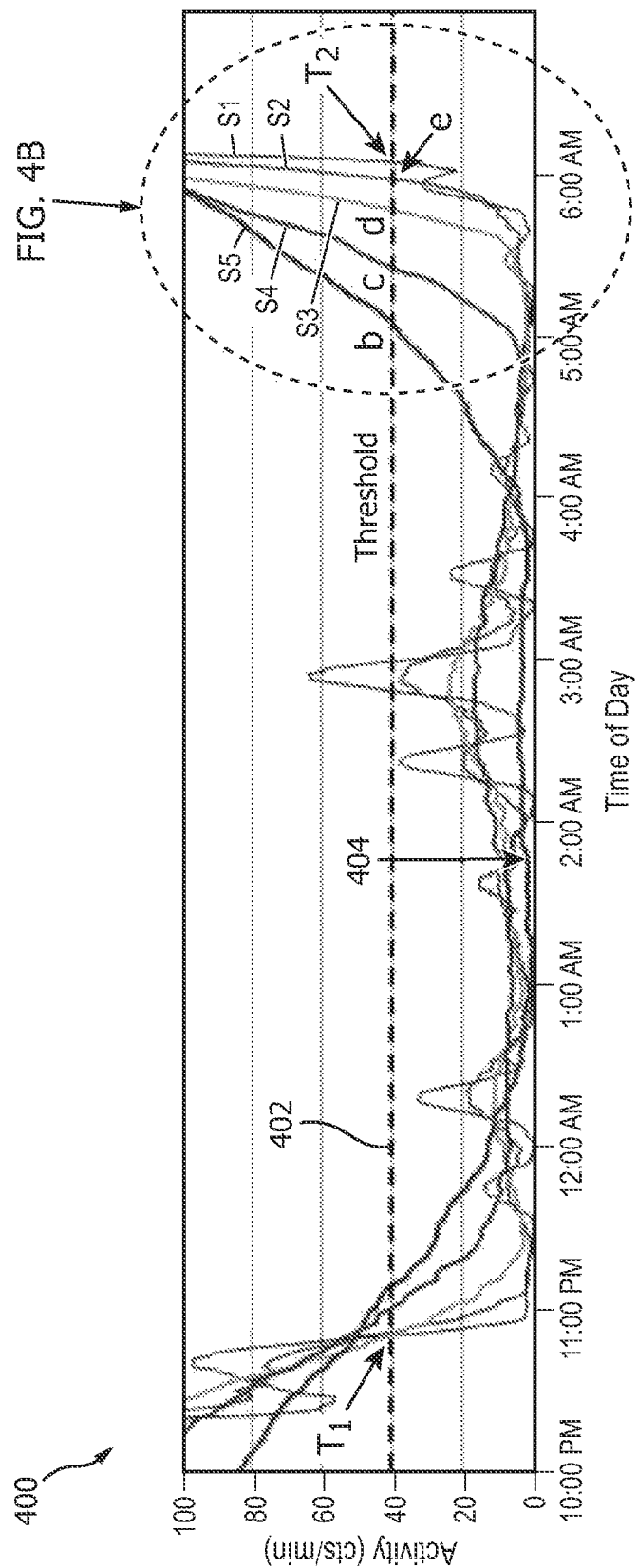
FIG. 4A is an illustrative graph of a portion of the exemplary model data of FIG. 3 corresponding to a rest period, in accordance with various embodiments.

FIG. 4A is an illustrative graph 400 of a portion of the exemplary model data of FIG. 3 corresponding to a rest period, in accordance with various embodiments. In the illustrative embodiment, graph 400 corresponds to an exemplary "rest period" of the motion data. The rest period corresponds to a period of time where motion is at a minimum; typically corresponding to when an individual is sleeping. In one exemplary embodiment, motion data is received, and the motion data is processed to develop five representations (e.g., curves S1-S5) of the raw motion data (e.g., activity values versus time). The minimum value of a first representation is the starting point for the process. Moving both forward and backward in time from this minimum time identifies two intersections of a horizontal line set at a threshold activity values. These are the first two approximations of a beginning and an end of the rest period. These first approximations are then used as starting points on the second representation, and the process is repeated through a third, fourth, and fifth representation, and then for the original data, to provide a final values for the beginning and end of the rest period.

Graph 400 includes a threshold activity level 402, which defines whether a certain amount of activity corresponds to an active period or a rest period. In one embodiment, motion data that exceeds threshold activity level 402 would correspond to an active period, while motion data that is below threshold activity level 402 would correspond to a rest period. Threshold activity level 402 is defined prior to, or during, analysis of an amount of time of a rest period. For example, threshold activity level 402 may be set as being 40 counts/minute, however threshold activity level 402 may be adjusted after a rest period has been calculated to determine an effect on the duration of the rest period that the threshold activity level has. An optimal threshold activity level may also be determined, using various techniques, which are described in greater detail below.

As seen within graph 400, a first data set represented by curve S5, a second data set represented by curve S4, a third data set represented by curve S3, a fourth data set represented by curve S2, and a fifth data set represented by curve S1 are all presented. Curve S5 corresponds to a moving Gaussian window having a length of 100 minutes is the most heavily "smoothed" curve, having been applied to the raw motion data. One or more local minima of the S5 curve correspond to a potential rest period. For example, a minimum point 404 of curve S5 corresponds to a minimum value of the motion data.

Figure 4B:
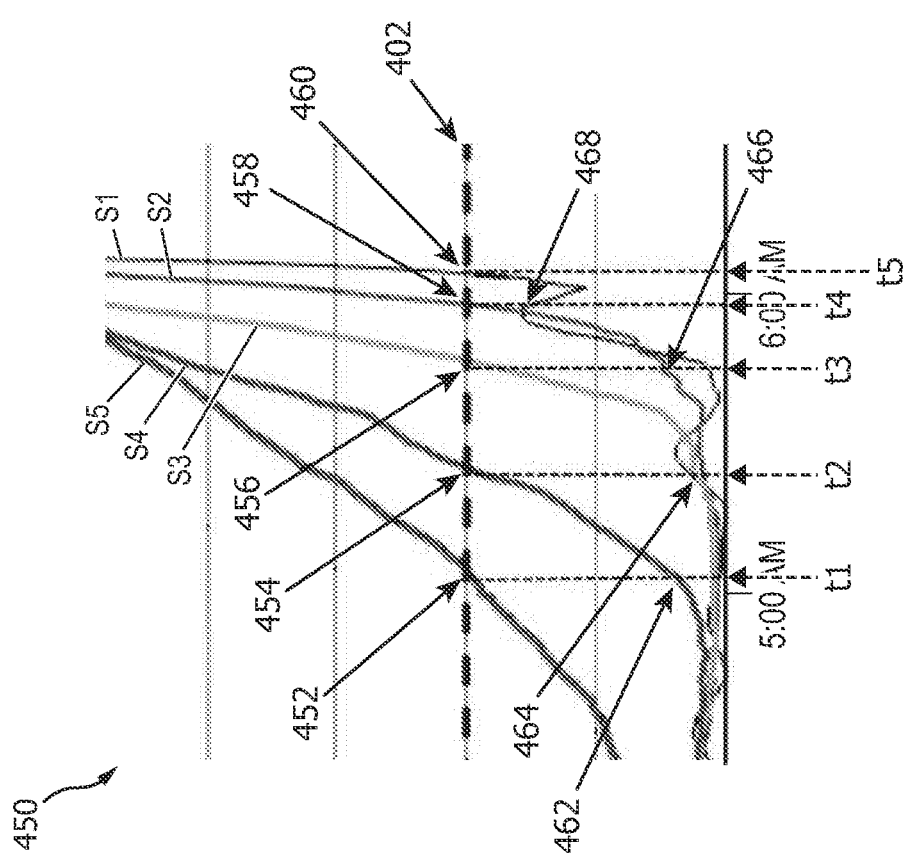
FIG. 4B is an illustrative graph of a portion of the exemplary model data of FIG. 4A corresponding to an end of the rest period, in accordance with various embodiments.

To identify an end of a rest period, such as the rest period shown within graph 400, an iterative process is used to find an upper boundary of the rest period. FIG. 4B is an illustrative graph 450 of a portion of the exemplary model data of FIG. 4A corresponding to an end of the rest period, in accordance with various embodiments. In particular, graph 450 of FIG. 4B corresponds to an upper region (e.g., end portion) of a rest period shown within graph 400 of FIG. 4A. First, to identify an end time of the rest period of graph 400, minimum point 404 is determined.

Starting from minimum point 404 on curve S5, an upper intersection point 452 between threshold activity level 402 and curve S5 is determined. Upper intersection point 452 is found, in one embodiment, by moving along curve S5, epoch by epoch, until curve S5 crosses threshold activity level 402. For example, at upper intersection point 452, curve S5 reaches the predefined threshold activity level 402 (e.g., 40 counts/minute). Upper intersection point 452 occurs to a time t1, which corresponds to a position 462 on curve S4, the next most heavily "smoothed" curve of curves S1-S5. After point 462 is determined, an upper intersection point 454 between threshold activity level 402 and curve S4 is determined. Upper intersection point 454 is found, in one embodiment, by moving along curve S4, epoch by epoch, until curve S4 crosses threshold activity level 402. For example, at upper intersection point 454, curve S4 reaches the predefined threshold activity level 402 (e.g., 40 counts/minute). Upper intersection point 454 occurs at a time t2, which corresponds to a position 464 on curve S3, the next most heavily "smoothed" curve of curves S1-S5. After position 464 is determined, an upper intersection point 456 between threshold activity level 402 and curve S3 is determined. Upper intersection point 456 is found, in the illustrative embodiment, by moving along curve S3, epoch by epoch, until curve S3 crosses threshold activity level 402. For example, at upper intersection point 456, curve S3 reaches the predefined threshold activity level 402 (e.g., 40 counts/minute). Upper intersection point 456 occurs at a time t3, which corresponds to a position 466 on curve S2, the next most heavily "smoothed" curve of curves S1-S5. After position 466 is determined, an upper intersection point 458 between threshold activity level 402 and curve S2 is determined. Upper intersection point 458 is found, in the illustrative embodiment, by moving along curve S2, epoch by epoch, until curve S2 crosses threshold activity level 402. For example, at upper intersection point 458, curve S2 reaches the predefined threshold activity level 402 (e.g., 40 counts/minute). Upper intersection point 458 occurs at a time t4, which corresponds to a position 468 on curve S1, the least "smoothed" curve of curves S1-S5. After position 468 is determined, an upper intersection point 460 between threshold activity level 402 and curve S1 is determined. Upper intersection point 460 is found, in the illustrative embodiment, by moving along curve S1, epoch by epoch, until curve S1 crosses threshold activity level 402. For example, at upper intersection point 460, curve S1 reaches the predefined threshold activity level 402 (e.g., 40 counts/minute). Upper intersection point 460 occurs at a time t5. The position on the motion data of graph 200 corresponding to time t5 is then determined, after which a raw data upper intersection point where the motion data intersects with threshold activity level 402. The raw data upper intersection point is found, for example, by moving along the motion data, epoch by epoch, until the raw motion data cross threshold activity level 402. A raw upper time, when the raw data upper intersection point occurs, is then determined. The raw upper time is then set as an upper boundary of the rest period.

As similar technique is performed for to identify a start time of the rest period of graph 400, using minimum point 404. In this particular scenario, a raw data lower intersection point, where the motion data intersects with threshold activity level 402, is determined. The raw data lower intersection is found, for example, by determining the various lower intersection points of each of curves S1-S5, in order to accurately determine a location of the raw data lower intersection point. After the raw data lower intersection point is found, a raw lower time, when the raw data lower intersection point occurs, is then determined. The raw lower time is then set as a lower boundary of the rest period.

After both the raw upper time and the raw lower time are determined, a temporal difference between these two times is calculated. The temporal difference, therefore, corresponds to an amount of time of the rest period. Furthermore, in one embodiment, regions of the motion data, such as the motion data of graph 200, which are not within the rest period are classified as being active periods. In one embodiment, the motion data includes multiple (e.g., two or more) rest periods. In this particular scenario, a similar process to that described above is performed to determine a start time and an end time of each rest period. Furthermore, persons of ordinary skill in the art will recognize that although five data sets represented by curves S1-S5 are generated by applying five moving Gaussian windows of differing lengths to the raw motion data, any number of filters producing any number of data sets may be used, and the aforementioned is merely one illustrative example. Additionally, a moving Gaussian window is just one exemplary processing technique that may be employed, and any other suitable filter or processing technique, such as a rectangular window, or combination of filters, may be employed.

Figure 5:
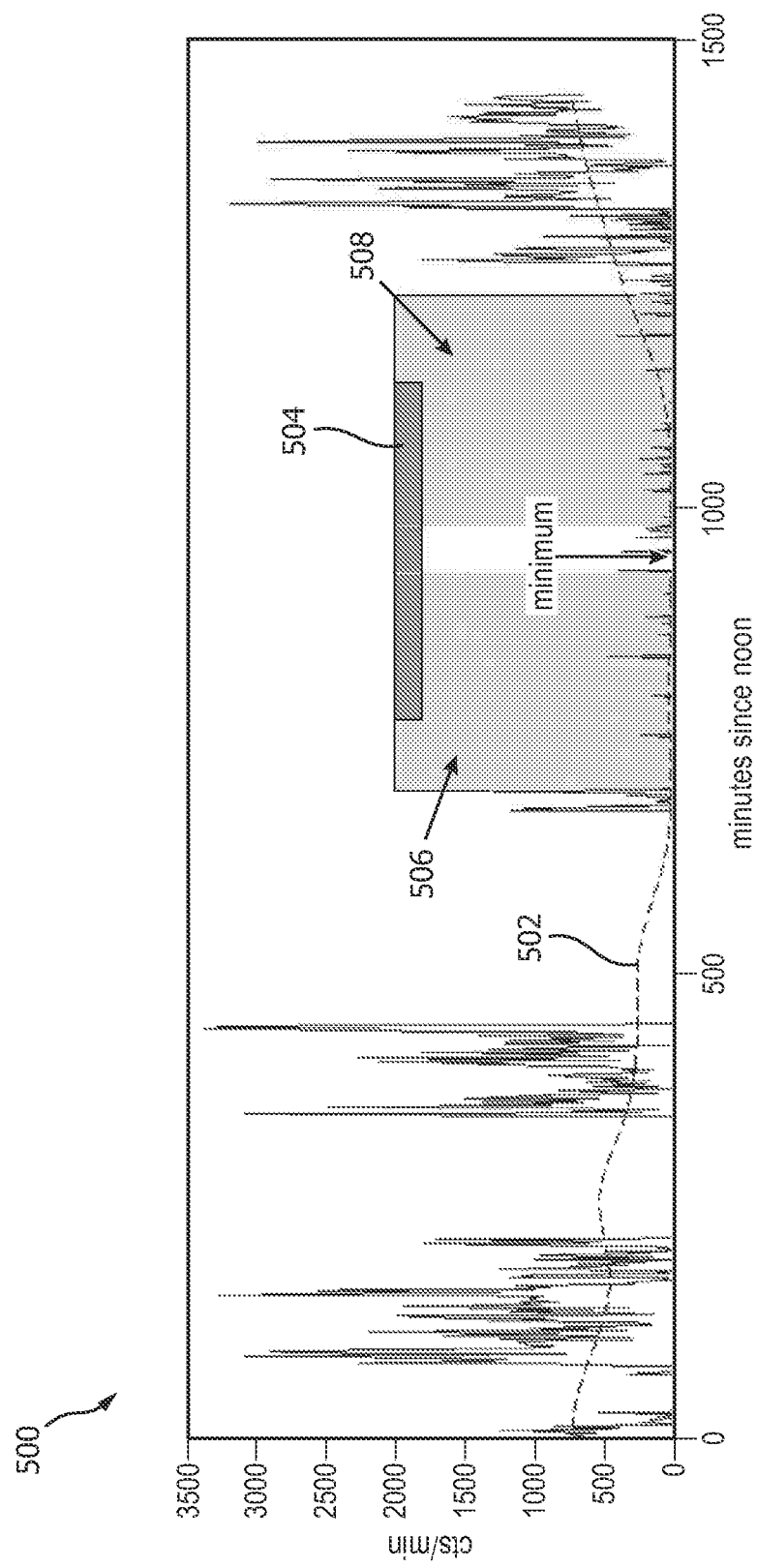
FIG. 5 is an illustrative graph of the exemplary motion data of FIG. 2 including a generated data set, in accordance with various embodiments.
Figure 6A:
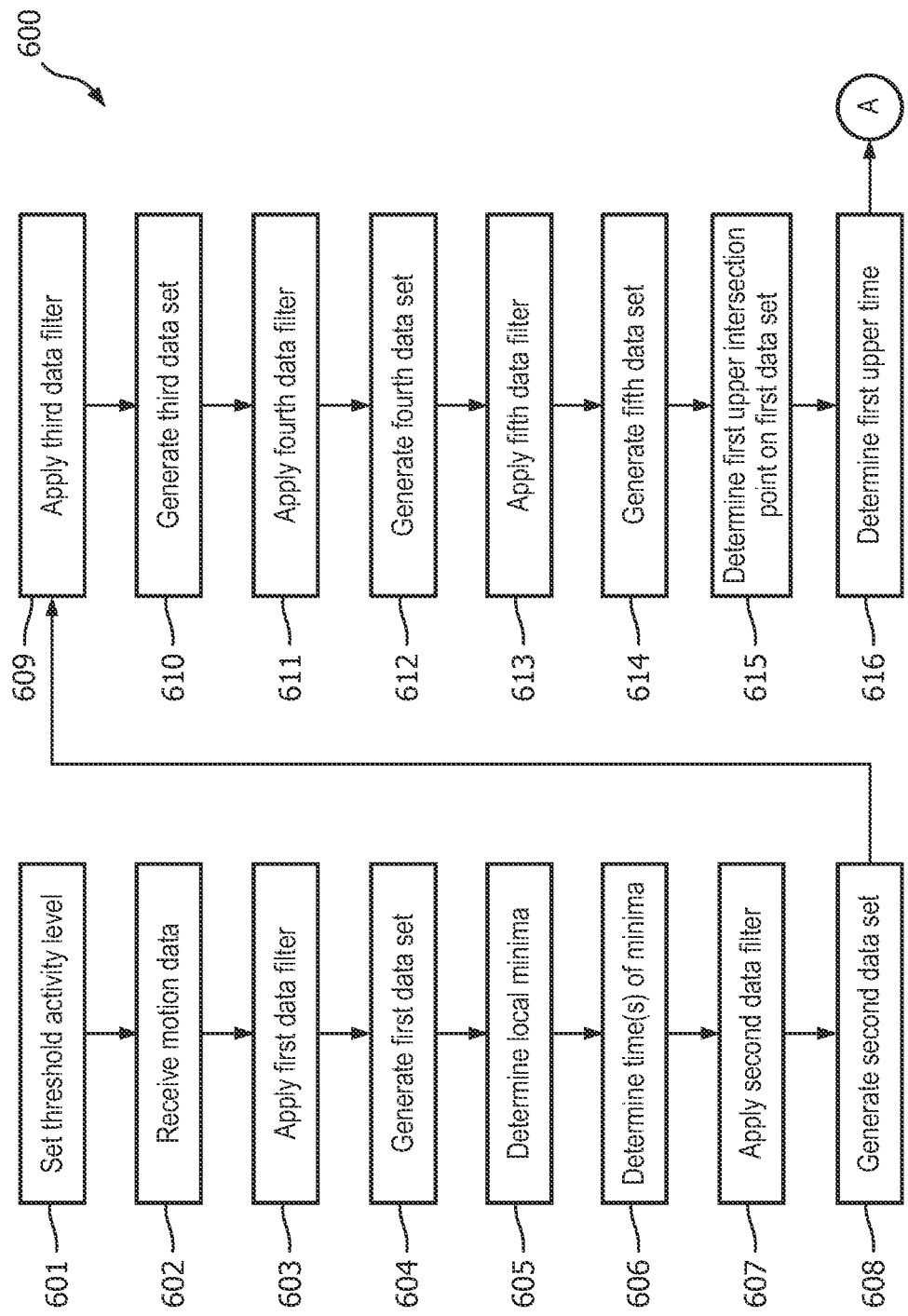
FIGS. 6A-D is an illustrative flowchart of a process for determining an amount of time of a rest period, in accordance with various embodiments.
Figure 6B:
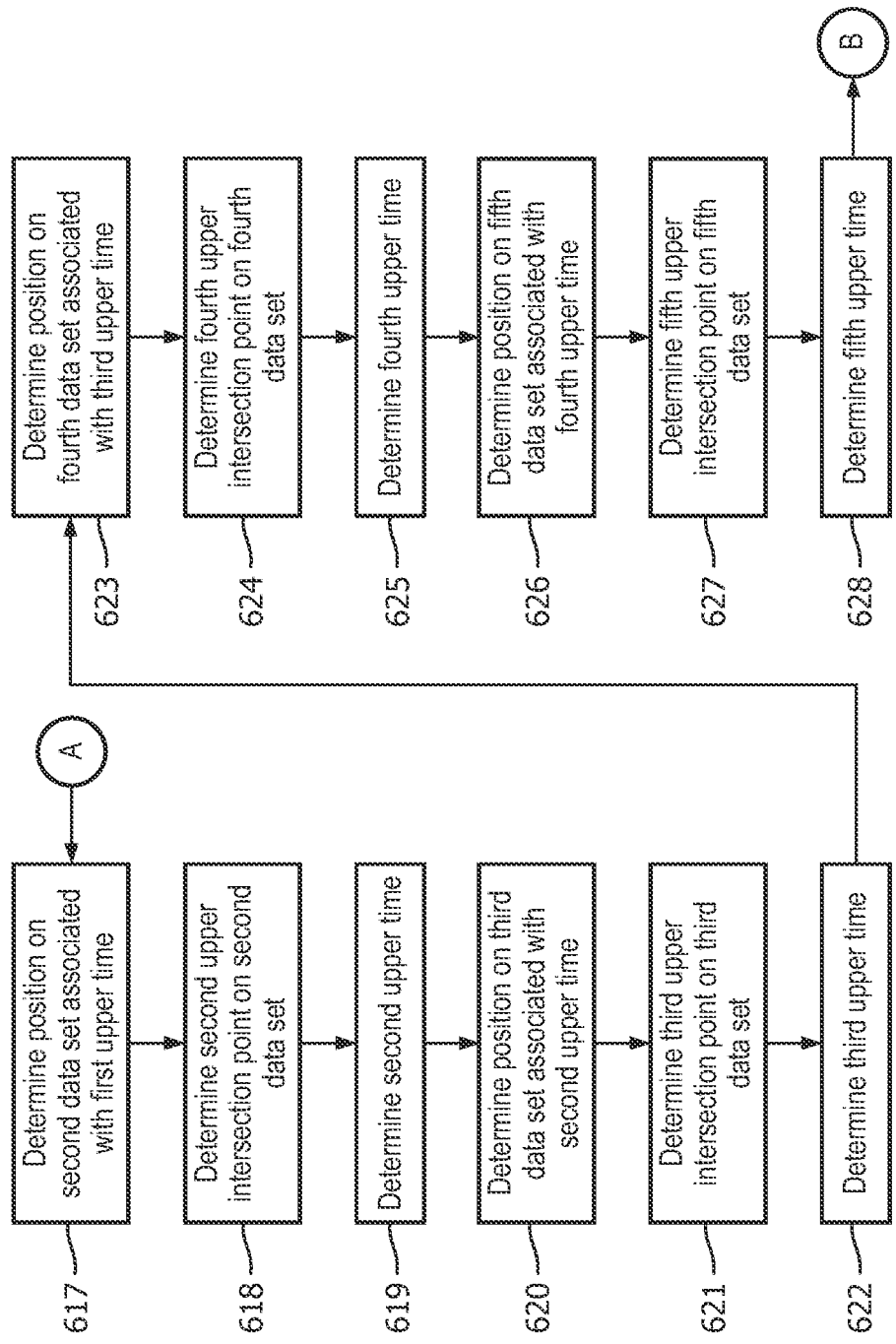
Figure 6C:
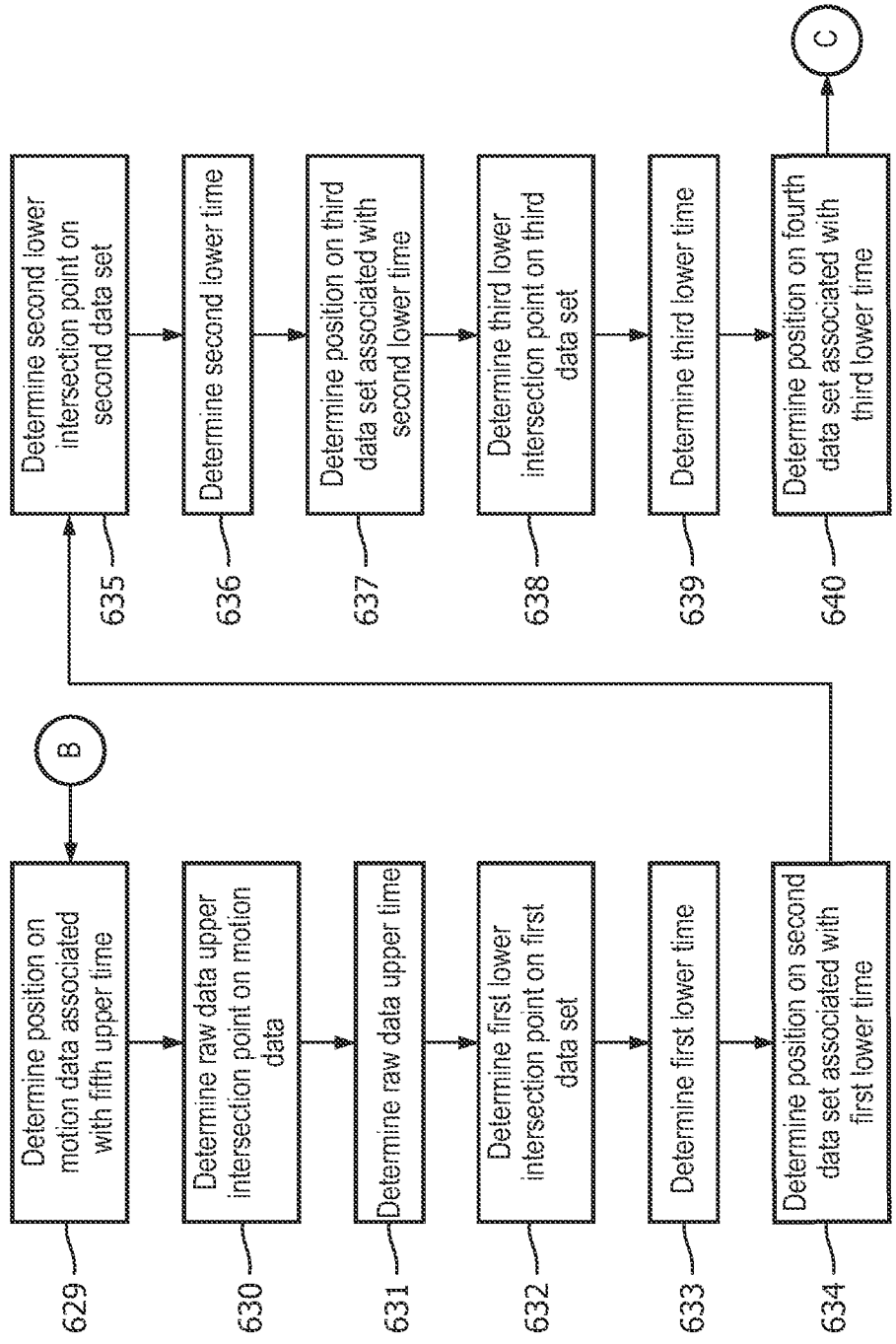
Figure 6D:
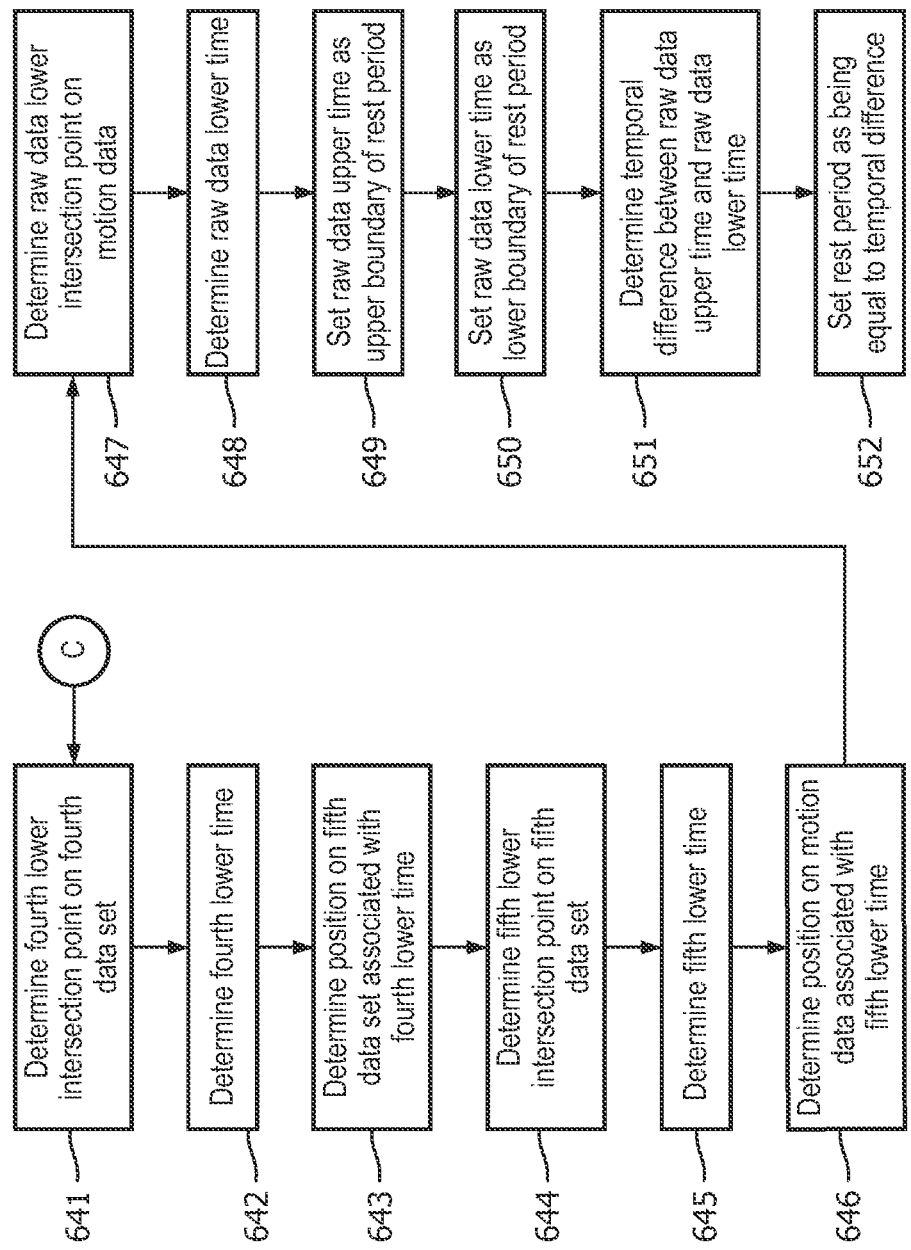

FIG. 5 is an illustrative graph 500 of the exemplary motion data of FIG. 2 including a generated data set, in accordance with various embodiments. Graph 500, in the illustrative, non-limiting embodiment, includes motion data, such as the raw motion data of FIG. 2, presented in terms of minutes since noon (e.g., 12:00 PM) on the x-axis, and counts per minute (e.g., counts/minute) on the y-axis. One issue that potentially can arise in accurately determining a temporal duration of a rest period is an errant active period that occurs within the rest period. For example, if an individual gets out of bed during the night for even a few minutes, this may register as an active period. Thus, a rest period may, mistakenly, be identified as two shorter rest periods separated by a brief active period, and therefore a total temporal duration of a rest period may appear shorter than it actually is.

In order to avoid such potential discrepancies, in one embodiment, an expected rest period length is selected, and a moving Gaussian window having a length of the expected rest period is applied to the motion data. For example, an expected rest period of approximately 6 hours, or 360 minutes, may be selected, and a moving Gaussian window having a length of 360 minutes may be applied to the motion data. Thus, in this particular scenario, a data set of the motion data is generated, which is represented by a curve 502, for instance by having a moving Gaussian window with length 360 minutes applied thereto. A major rest period 504, in the illustrative embodiment, is therefore identified as a period of time with which curve 502 registers activity below a predefined threshold activity level (e.g., 40 counts/minute). This causes a first rest period 506 and a second rest period 508 to be joined together as major rest period 504, such that any minor activity occurring during major rest period 504 does not separate out major rest period 504 into first rest period 506 and second rest period 508.

FIGS. 6A-D is an illustrative flowchart of a process for determining an amount of time of a rest period, in accordance with various embodiments. Process 600, in one embodiment, begins at step 601. At step 601, a threshold activity level is set. For example, threshold activity level 402 of FIG. 4A may be selected for the threshold activity level. As mentioned previously, the threshold activity level corresponds to a value with which any activity that does not exceed this level is determined to correspond to a rest period. In one exemplary embodiment, an optimal threshold activity level is selected for use as the threshold activity level, and the process for selecting the optimal threshold activity level is described in greater detail below with reference to FIG. 8.

At step 602, motion data is received from one or more motion sensors. For example, motion data recorded by motion sensors 110 on wearable motion tracker 150 may be received by motion analysis device 100. The motion data, in an exemplary embodiment, corresponds to an amount of activity that was captured by motion sensor(s) 110 for an individual during the course of a day (e.g., 24 hours). However, any suitable time period for capturing motion data may be used, such as a day, a week, a month, or longer.

At step 603, a first data filter is applied to the motion data. For example, a moving Gaussian window may be applied to the motion data. In one embodiment, the application of the first data filter generates a data set represented by a most heavily smoothed curve. As one illustrative example, the first data filter may be a moving Gaussian window having a length equal to an expected temporal length of a rest period, such as 360 minutes. As another illustrative example, the first data filter may be a moving Gaussian window, such as a moving Gaussian window having a length of 100 minutes. At step 604, a first data set representing the motion data is generated in response to the first data filter being applied to the motion data. For example, curve 502 of FIG. 5 may be generated in response to a moving Gaussian window having a length of 360 minutes being applied to the motion data of graph 200 of FIG. 2. As another example, curve S5 of FIG. 4A may be generated in response to a moving Gaussian window having a length of 100 minutes being applied to the motion data of graph 200.

At step 605, one or more local minima of the generated first data set are determined. A second derivative of the first data set, in one embodiment, is calculated to determine points along the first data set representative of a minimum, however any suitable minimization technique is capable of being employed. As an illustrative example, minimum point 404 of FIG. 4A may correspond to a local minimum of a respectively most heavily smoothed data curve. At step 606, a time associated with the minimum point, or points, is determined. For example, minimum point 404 of FIG. 4A occurs at an approximate time of 1:45 AM.

At step 607, a second data filter is applied to the originally received motion data (e.g., raw motion data), and, at step 608, a second data set representing the motion data is generated. For example, a moving Gaussian window having a length of 80 minutes may be applied to the motion data, and another data set represented by a next most heavily smoothed curve, curve S4, may be generated for the motion data. At step 609, a third data filter is applied to the originally motion data, and, at step 610, a third data set is generated. For example, a moving Gaussian window having a length of 60 minutes may be applied to the raw motion data, and another data set represented by a next most heavily smoothed curve, curve S3, may be generated for the motion data. At step 611, a fourth data filter is applied to the originally received motion data, and, at step 612, a fourth data set is generated. For example, a moving Gaussian window having a length of 40 minutes may be applied to the raw motion data represented by as a next most heavily smoothed curve, curve S2, may be generated for the motion data. Furthermore, at step 613, a fifth data filter is applied to the originally received motion data, and, at step 614, a fifth data set is generated. For example, a moving Gaussian window having a length of 20 minutes may be applied to the motion data, and another data set represented by a least most heavily smooth curve, S1, may be generated for the motion data. Persons of ordinary skill in the art will recognize that any ordering for processing, such as data smoothing, data and thereby generating a data set may be employed by process 600, and serially processing the motion data is merely exemplary. For example, all five data sets may be generated in parallel by processing the motion data five different times to the motion data at a same time. Furthermore, processing data need not occur from most heavily smoothed to least heavily smoothed, and any ordering of processing data may be used. Still further, in one embodiment, the determination of the local minima, and the local minima associated time(s), as well as the setting of the threshold activity level, may occur before any data sets are generated by applying a data filter, after any data sets are generated, or prior to some data sets being generated but after others, and the ordering sequence of process 700 is merely illustrative.

Steps 615-631 correspond to an iterative process for objectively determining an upper boundary of a rest period. At step 615, a first upper intersection point, where the first data set intersects with the threshold activity level, is determined. The first upper intersection point is found, in the illustrative embodiment, by starting at the minimum point (e.g., minimum point 404), and advancing forward in time along the first data set (e.g., the S5 curve), until the first data set reaches the threshold activity level. As an illustrative example, curve S5 intersects with threshold activity level 402 at first upper intersection point 452. After the first upper intersection point is determined, a first upper time associated with the first upper intersection point is determined at step 616. For example, first upper intersection point 452 occurs at time t1.

After the first upper time is determined at step 616, a position on the second data set that is associated with the first upper time is determined at step 617. For example, position 462 on curve S4 corresponds to time t1. At step 618, the second data set is followed until a second upper intersection point, where the second data set intersects with the threshold activity level, is determined. For example, curve S4 may be followed until reaching second upper intersection point 454, where curve S4 intersects with threshold activity level 402. A second upper time (e.g., time t2), associated with the second upper intersection point is determined at step 619, and a position on the third data set associated with the second upper time is determined at step 620. For example, second upper intersection point 454 occurs at time t2, and position 464 is the corresponding position at time t2 of curve S3.

At step 621, a third upper intersection point is determined by following the third data set from the position on the third data set associated with the second upper time, to a third upper intersection point where the third data set intersects with the threshold activity level. For example, starting from point 464, curve S3 is followed until third upper intersection point 456. A third upper time, such as time t3, associated with where the third data set intersects with the threshold activity level is determined at step 622. Next, a position along the fourth data set associated with the third upper time, (e.g., time t3), is determined at step 623. For example, position 466 on curve S2 is the corresponding position at time t3 of curve S2.

At step 624, a fourth upper intersection point is determined by following the fourth data set from the position on the fourth data set associated with the third upper time, to a fourth upper intersection point where the fourth data set intersects with the threshold activity level. For example, starting from point 466, curve S2 is followed until fourth upper intersection point 458. A fourth upper time, such as time t4, associated with where the fourth data set intersects with the threshold activity level is determined at step 625. Next, a position along the fifth data set associated with fourth upper time, (e.g., time t4) is determined at step 626. For example, position 468 on curve S1 is the corresponding position at time t4 of curve S1.

At step 627, a fifth upper intersection point is determined by following the fourth data set from the position on the fifth data set associated with the fourth upper time, to a fifth upper intersection point where the fourth data set intersects with the threshold activity level. For example, starting at point 468, curve S1 is followed until fifth upper intersection point 460. A fifth upper time, such as time t5, associated with where the fifth data set intersects with the threshold activity level is determined at step 628. Next, a position along the raw motion data (e.g., motion data presented within graph 200), associated with the fifth upper time (e.g., time t5) is determined at step 629. The position along the raw motion data is then followed forward until the raw motion data intersects with the threshold activity level (e.g., threshold activity level 402). This, in one embodiment, corresponds to a raw data upper intersection point, which is determined at step 630. A time when the raw data upper intersection point occurs, the raw data upper time, is then determined at step 631. Using this iterative process, a substantially objective and uniform procedure for determining an upper bound of the rest period is able to be determined. Instead of using just the raw motion data, which includes various spikes and abnormalities, the various data sets that were generated allow for a precise approximation of the upper boundary of the rest period such that an accurate position where the raw data crosses the threshold activity level, signifying the end of the rest period, can be determined systemically. This determination is extremely difficult, if not impractical, to determine using standard, manual, techniques because the data sets are too large to analyze using conventional, manual procedures.

Steps 632-648 correspond to a substantially similar process as that of steps 615-631, except that steps 632-648 correspond to a determination of a lower boundary of the rest period. At step 632, a first lower intersection point, where the first data set intersects with the threshold activity level is determined. The first lower intersection point is found, in the illustrative embodiment, by starting at the minimum point (e.g., minimum point 404), and advancing backward in time along the first data set (e.g., represented by curve S5), until the first data set reaches threshold activity level 402. After the first lower intersection point is determined, a first lower time associated with the first lower intersection point is determined at step 633.

After the first lower time is determined, a position on the second data set, (e.g., represented by curve S4), that is associated with the first lower time is determined at step 634. At step 635, the second data set is followed until a second lower intersection point, where the second data set intersects with the threshold activity level is determined. A second upper time, associated with the second lower intersection point, is determined at step 636, and a position on the third data set, (e.g., curve S3), associated with the second lower time is determined at step 637.

At step 638, a third lower intersection point is determined by following the third data set (e.g., represented by curve S3) from the position on the third data set associated with the second lower time to where the third data set intersects with the threshold activity level. A third lower time associated with the third lower intersection point, (e.g., where curve S3 intersects with threshold activity level 402), is determined at step 639. Next, a position along the fourth data set, (e.g., represented by curve S2), associated with the third lower time is determined at step 640.

At step 641, a fourth lower intersection point is determined by moving back along the fourth data set from the position along the fourth data set that is associated with the third lower time to where the fourth data set intersects with the threshold activity level (e.g., threshold activity level 402). A fourth lower time, associated with the fourth lower intersection point, is determined at step 642. Next, a position along the fifth data set (e.g., curve S1) associated the fourth lower time is determined at step 643. At step 644, a fifth upper intersection point is determined by moving back along the fifth data set from the position along the fifth data set associated with the fourth lower time to where the fifth data set intersects with the threshold activity level. A fifth lower time associated with the fifth lower intersection point, (e.g., where curve S1 intersects with threshold activity level 402), is determined at step 645.

Next, a position along the raw motion data (e.g., motion data presented within graph 200), associated with the fifth lower time, is determined at step 646. The position along the raw motion data is then followed backwards along the raw motion data until the raw motion data intersects with the threshold activity level. This, in one embodiment, corresponds to a raw data lower intersection point, which is determined at step 647. A raw data lower time when the raw data lower intersection point occurs is then determined at step 648.

At step 649, the raw data upper time determined at step 631 is set as being the upper boundary of the rest period. At step 650, the raw data lower time determined at step 648 is set as being the lower boundary of the rest period. Using the upper and lower boundaries of the rest period, a temporal difference between the raw data upper time and the raw date lower time is determined at step 651. For example, if a raw data upper time corresponds to 6:00 AM, and a raw data lower time corresponds to 11:00 PM the previous day, then the temporal difference between the raw data upper time and the raw data lower time would be 7:00 hours, or 420 minutes. At step 652, a temporal duration of the rest period is set as being the temporal difference. Continuing the previous example, a temporal duration of the rest period would, therefore, be 7:00 hours or 420 minutes. Process 600, therefore, provides a useful measurement technique for actigraphy data to identify sleep periods and active periods of an individual. Process 600 further provides a substantially precise identification of motion biomarkers that is both efficient for large data sets, as well as being objective.

Figure 7:
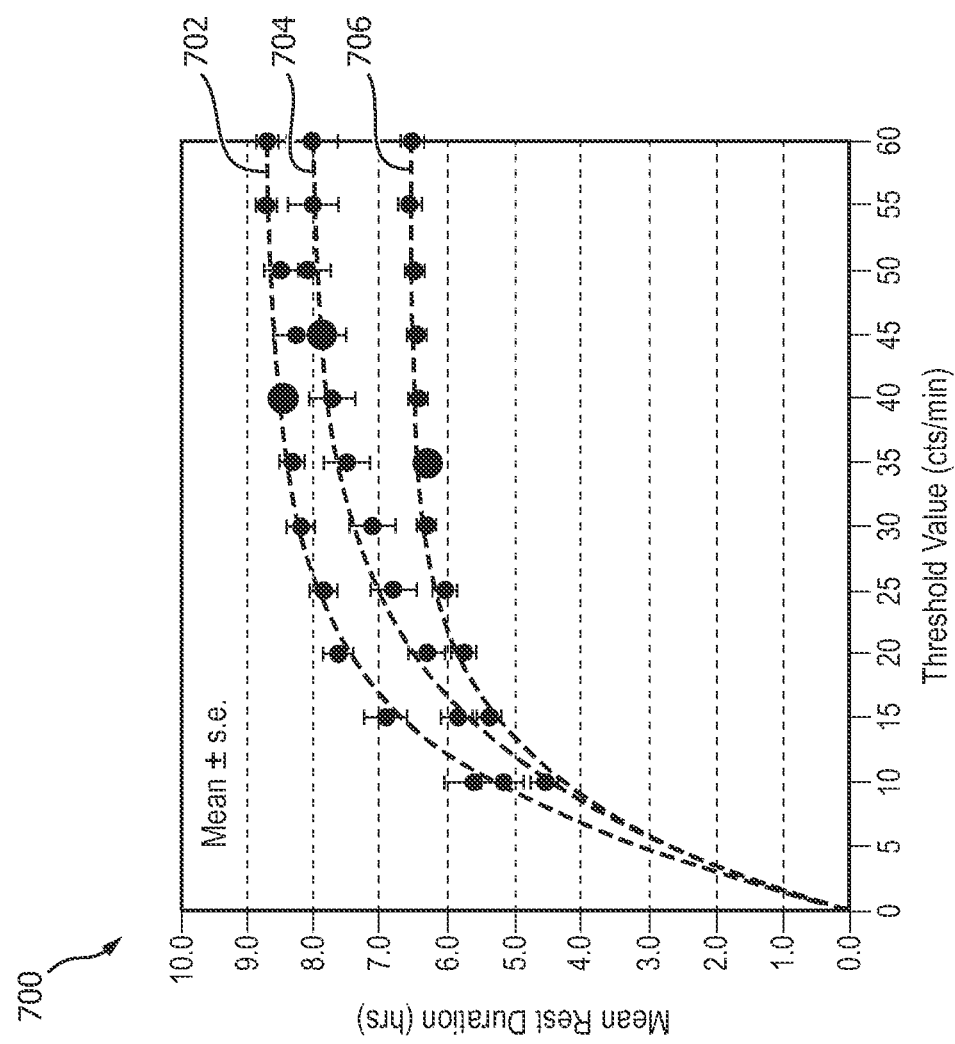
FIG. 7 is an illustrative graph of a relationship between a mean rest period and a threshold activity level, in accordance with various embodiments.

FIG. 7 is an illustrative graph 700 of a relationship between a mean rest period and a threshold activity level, in accordance with various embodiments. Graph 700 corresponds to a technique for selecting an optimal threshold activity level, such as threshold activity level 402 of FIG. 4A. In graph 700, various values for the threshold activity level, in counts per minute, are provided on the x-axis, while a mean temporal duration of the rest period, whose calculation is described above, is provided on the y-axis. As seen within graph 700, a line 702, a line 704, and a line 706 are each plotted, representing three different sets of motion data. As the threshold activity level is increased from 10 counts/minute to 80 counts/minute, the mean rest period also increases. However, at a certain point, the mean rest period duration begins to flatten out and not increase.

The optimal threshold activity level, in one embodiment, is a threshold activity level that maximizes a temporal duration of the rest period, while also preventing inclusion of active periods therein that would otherwise increase the mean activity level of the rest period. Using the techniques for determining a temporal duration of the rest period, as described in greater detail above, the temporal duration of the rest period is determined for a first threshold activity level, and then the process is repeated for an increased threshold activity level. For example, a temporal duration of a rest period is calculated for a threshold activity level of 10 counts/minute. Next, a new temporal duration of the rest period is determined for a threshold activity level of 15 counts/minute. This process is then repeated, in the illustrative example, in increments of 5 counts/minute, until the threshold activity level is 60 counts/minute.

After the rest periods are determined, the optimal fit data is plotted with a simple exponential, as seen in Equation 1:

$$\text{Duration} = \text{Duration}_{Max}(1-e^{-kt}) \quad \text{Equation 1.}$$

In Equation 1, $\text{Duration}_{Max}$ is a maximum temporal duration of a rest period, t is a threshold value, and k is selected to minimize a sum of the squares of the error. In one exemplary embodiment, an optimal threshold activity value is selected by determining a value of t corresponding to 98% of $\text{Duration}_{Max}$, and rounding that value to the nearest 5 counts/minute.

Figure 8:
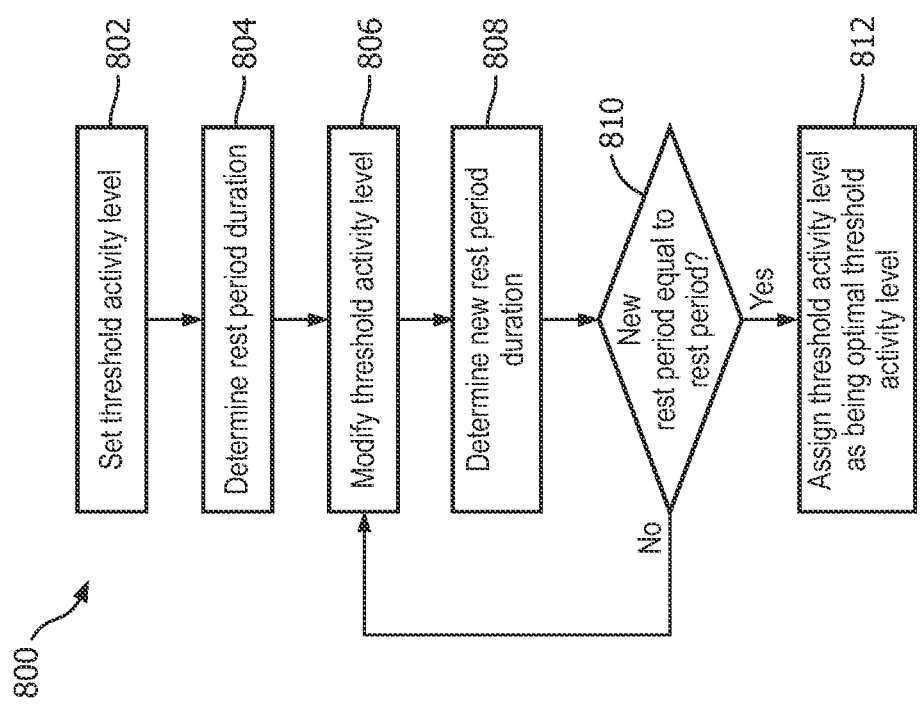
FIG. 8 is an illustrative flowchart of a process for selecting an optimal threshold activity level, in accordance with various embodiments.

FIG. 8 is an illustrative flowchart of a process 800 for selecting an optimal threshold activity level, in accordance with various embodiments. Process 800, in one embodiment, is used in conjunction with some or all of process 600 of FIG. 6. For example, process 600 may be used to obtain a temporal duration of a rest period for a particular threshold activity level. Process 800 begins at step 802 in one embodiment. At step 802, a threshold activity level is set. As mentioned above with regards to step 606 of process 600, an initial threshold activity level is set. For example, a first threshold activity level of 10 counts/minute may be set as an initial threshold activity level. A user of motion analysis device 100 programs the initial threshold activity level, in one embodiment, however a manufacturer may alternatively program the initial threshold activity level. At step 804, a temporal duration of the rest period for the initial threshold activity level is determined (e.g., using process 600 of FIG. 6).

At step 806, the threshold activity level is modified. For example, if the previous threshold activity level was 10 counts/minute, a new threshold activity level may be set as 15 counts/minute. Using the new threshold activity level, a temporal duration of a new rest period is determined at step 808. For example, process 600 of FIG. 6 may be used to calculate a new temporal duration of a rest period using a new threshold activity level.

At step 810, a determination is made as to whether or not the temporal duration of the new rest period is equal to the temporal duration of the previous rest period. If, at step 810, it is determined that the new rest period's temporal duration is not equal to the previous rest period's temporal duration, process 800 returns to step 806, where the threshold activity level is once again modified. For example, the threshold activity level may now be increased from 15 counts/minute to 20 counts/minute. Next, another new rest period temporal duration is determined, and this is again compared with the previous rest period's temporal duration at step 808. This loop is repeated until a substantially same rest period duration is determined for at least threshold activity levels. For instance, if two threshold activity levels yield a substantially similar rest period temporal duration, then process 800 has most likely identified an optimal threshold activity level to be used. However, multiple loops having similar rest period duration for different threshold activity levels may provide more accurate measurements of the optimal threshold activity level, defined for example, by Equation 1.

If, at step 810, it is determined that the previously calculated rest period's temporal duration is equal to the currently calculated rest period's temporal duration, then, as mentioned previously, process 800 proceeds to step 812. At step 812, the threshold activity level used previously, or the new or modified threshold activity level, is assigned as being the optimal threshold activity level. Typically, if two threshold activity levels both produce a substantially same rest period temporal duration, then the optimal threshold activity level is selected as being the lesser of the two, however either threshold activity level is capable of being selected.

In one embodiment, after the temporal durations of the rest period are determined for each different threshold activity level, the data is fit using the data model of FIG. 1. An optimal threshold activity level is then obtained from the fit coefficients. This enables the optimal threshold activity level to be obtained for each data set, and, consequently, for use in future data analysis.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method for identifying a rest period of an individual, the method comprising:
    setting a threshold activity level for the rest period to an initial threshold activity level, wherein the threshold activity level is expressed in terms of an activity count during each epoch of a given temporal duration;
    receiving motion data, via a wearable motion tracker having a least one motion sensor, representative of an amount of activity in terms of the activity count during each epoch of the given temporal duration experienced by the individual over a course of a given time interval greater than the given temporal duration;
    applying at least a first data filter and a second data filter, different from the first data filter, to the motion data to generate at least a first data set and a second data set different from the first data set, representative of the motion data;
    determining a minimum point within the first data set;
    determining a minimum time within the given time interval associated with the minimum point;
    determining an upper boundary of the rest period, via the steps of:
        determining a first upper intersection point where the first data set intersects with the threshold activity level, wherein the first upper intersection point occurs after the minimum time;
        determining a first upper time within the given time interval associated with the first upper intersection point, the first upper time corresponding to a first approximation of the upper boundary of the rest period;
        determining a second upper intersection point where the second data set intersects with the threshold activity level based on the first upper time being used as a starting point for determining the second upper intersection point;
        determining a second upper time within the given interval associated with the second upper intersection point, the second upper time corresponding to a second approximation of the upper boundary of the rest period;
        determining a first position on the motion data corresponding to the second upper time;
        determining a raw data upper intersection point where the motion data intersects with the threshold activity level based on the second upper time being used as a starting point for determining the raw data upper intersection point, wherein the raw data upper intersection point occurs within the motion data after the first upper time;
        determining a raw data upper time within the given time interval associated with the raw data upper intersection point, wherein the raw data upper time occurs after the first upper time within the rest period; and
        setting the raw data upper time as the upper boundary of the rest period;
    determining a lower boundary of the rest period, via the steps of:
        determining a first lower intersection point where the first data set intersects with the threshold activity level, wherein the first lower intersection point occurs prior to the minimum time;
        determining a first lower time within the given time interval associated with the first lower intersection point, the first lower time corresponding to a first approximation of the lower boundary of the rest period;
        determining a second lower intersection point where the second data set intersects with the threshold activity level based on the first lower time being used as a starting point for determining the second lower intersection point;
        determining a second lower time within the given interval associated with the second lower intersection point, the second lower time corresponding to a second approximation of the lower boundary of the rest period;
        determining a second position on the motion data corresponding to the second lower time;
        determining a raw data lower intersection point where the motion data intersects with the threshold activity level based on the second lower time being used as a starting point for determining the raw data lower intersection point, wherein the raw data lower intersection point occurs in the motion data prior to the first lower time;
        determining a raw data lower time within the given time interval associated with the raw data lower intersection point, wherein the raw data lower time occurs before the first lower time within the rest period; and
        setting the raw data lower time as the lower boundary of the rest period; and
    determining an amount of time of the rest period, identified via the upper boundary of the rest period and the lower boundary of the rest period, by calculating a temporal difference between the raw data upper time and the raw data lower time.

2. The method of claim 1, wherein:
the motion data comprises a plurality of data points; and
the plurality of data points are representative of the amount of activity in terms of the activity detected during each epoch.

3. The method of claim 2, wherein a plurality of samples are obtained during each epoch, and the amount of activity during each epoch is an aggregate of the plurality of samples during a respective epoch.

4. The method of claim 1, wherein the first data filter comprises a moving Gaussian window of a first length of time and the second data filter comprises a moving Gaussian window of a second length of time, shorter than the first length of time.

5. The method of claim 1, wherein applying at least the first data filter and the second data filter, different from the first data filter further comprises:
applying a third data filter, different from the first and second data filters, to the motion data to generate a third data set representative of the motion data;
applying a fourth data filter, different from the first, second and third data filters, to the motion data to generate a fourth data set representative of the motion data; and
applying a fourth data filter, different from the first, second, third and fourth data filters, to the motion data to generate a fifth data set representative of the motion data,
wherein determining the upper boundary of the rest period further comprises:
determining respective third, fourth, and fifth upper intersection points where the third, fourth and fifth data sets intersect with the threshold activity level based on a respective second, third and fourth upper time being used as a starting point for determining the respective third, fourth and fifth upper intersection points;
determining respective third, fourth, and fifth upper times within the given time interval associated with the respective third, fourth and fifth upper intersection points, the respective third, fourth and fifth upper times corresponding to a respective third, fourth and fifth approximation of the upper boundary of the rest period;
determining the raw data upper intersection point where the motion data intersects with the threshold activity level based on the fifth upper time being used as a starting point for determining the raw data upper intersection point, wherein the raw data upper intersection point occurs within the motion data after the first upper time; and
wherein determining the lower boundary of the rest period further comprises:
determining respective third, fourth, and fifth lower intersection points where the third, fourth and fifth data sets intersect with the threshold activity level based on a respective second, third and fourth lower time being used as a starting point for determining the respective third, fourth and fifth lower intersection points;
determining respective third, fourth, and fifth lower times within the given time interval associated with the respective third, fourth and fifth lower intersection points, the respective third, fourth and fifth lower times corresponding to a respective third, fourth and fifth upper approximation of the lower boundary of the rest period;
determining the raw data lower intersection point where the motion data intersects with the threshold activity level based on the fifth lower time being used as a starting point for determining the raw data lower intersection point, wherein the raw data lower intersection point occurs within the motion data after the first lower time.

6. The method of claim 1, further comprising:
applying a moving Gaussian window to the motion data to generate an additional data set of the motion data, the moving Gaussian window having a length of 360 minutes;
determining at least two local minima of the additional data set;
determining that the minimum point is located between at least two of the local minima; and
determining that the minimum point is associated with the rest period.

7. The method of claim 1, further comprising:
repeating, for at least two different threshold activity levels, until a new determined rest period duration is equal to a previous determined rest period duration, the following:
modifying the threshold activity level to a modified threshold activity level greater than a previous threshold activity level;
determining a new rest period duration corresponding to the amount of time of the rest period based on the modified threshold activity level and the motion data;
comparing the new rest period duration with a previous determined rest period duration; and
responsive to the new determined rest period duration being equal to a previous determined rest period duration, selecting a lesser of two most recent modified threshold activity levels for use as an optimal threshold activity level in place of the initial threshold activity level.

8. A system comprising:
a wearable motion tracker comprising at least one motion sensor;
a motion analysis device comprising:
communications circuitry that receives motion data from the wearable motion tracker, wherein the motion data is representative of an amount of activity in terms of an activity count during each epoch of a given temporal duration experienced by the wearable motion tracker over a course of a given time interval greater than the given temporal duration;
memory that stores the motion data; and
at least one processor configured to:
set a threshold activity level for a rest period to an initial threshold activity level, wherein the threshold activity level is expressed in terms of the activity count during each epoch of the given temporal duration;
apply at least a first data filter and a second data filter, different from the first data filter, to the motion data to generate at least a first data set and a second data set different from the first data set, representative of the motion data;
determine a minimum point within the first data set;
determine a minimum time within the given time interval associated with the minimum point;
determine an upper boundary of the rest period, via the step of:

determining a first upper intersection point where the first data set intersects with the threshold activity level, wherein the first upper intersection point occurs after the minimum time;

determining a first upper time within the given time interval associated with the first upper intersection point, the first upper time corresponding to a first approximation of the upper boundary of the rest period;

determining a second upper intersection point where the second data set intersects with the threshold activity level based on the first upper time being used as a starting point for determining the second upper intersection point;

determining a second upper time within the given time interval associated with the second upper intersection point, the second upper time corresponding to a second approximation of the upper boundary of the rest period;

determining a first position on the motion data corresponding to the second upper time;

determining a raw data upper intersection point where the motion data intersects with the threshold activity level based on the second upper time being used as a starting point for determining the raw data upper intersection point, wherein the raw data upper intersection point occurs within the motion data after the first upper time;

determining a raw data upper time within the given time interval associated with the raw data upper intersection point, wherein the raw data upper time occurs before the first upper time within the rest period; and assigning the raw data upper time as being the upper boundary of the rest period;

determine a lower boundary of the rest period, via the steps of:

determining a first lower intersection point where the first data set intersects with the threshold activity level, wherein the first lower intersection point occurs prior to the minimum time;

determining a first lower time within the given time interval associated with the first lower intersection point, the first lower time corresponding to a first approximation of the lower boundary of the rest period;

determining a second lower intersection point where the second data set intersects with the threshold activity level based on the first lower time being used as a starting point for determining the second lower intersection point;

determining a second lower time within the given time interval associated with the second lower intersection point, the second lower time corresponding to a second approximation of the lower boundary of the rest period;

determining a second position on the motion data corresponding to the second lower time;

determining a raw data lower intersection point where the motion data intersects with the threshold activity level based on the second lower time being used as a starting point for determining the raw data lower intersection point, wherein the raw data lower intersection point occurs in the motion data prior to the first lower time;

determining a raw data lower time within the given time interval associated with the raw data lower intersection point, wherein the raw data lower time occurs before the first lower time within the rest period; and assigning the raw data lower time as the lower boundary of the rest period; and determine an amount of time of the rest period, identified via the upper boundary of the rest period and the lower boundary of the rest period, by calculating a temporal difference between the raw data upper time and the raw data lower time.

9. The system of claim 8, wherein the at least one processor of the motion analysis device is further configured to:

apply a third data filter, different from the first and second data filters, to the motion data to generate a third data set representative of the motion data;

apply a fourth data filter, different from the first, second and third data filters, to the motion data to generate a fourth data set representative of the motion data; and apply a fourth data filter, different from the first, second, third and fourth data filters, to the motion data to generate a fifth data set representative of the motion data.

10. The system of claim 9, wherein determining the upper boundary of the rest period further comprises:

determining respective third, fourth, and fifth lower intersection points where the third, fourth and fifth data sets intersect with the threshold activity level based on a respective second, third and fourth lower time being used as a starting point for determining the respective third, fourth and fifth upper intersection points;

determining respective third, fourth, and fifth upper times within the given time interval associated with the respective third, fourth and fifth upper intersection points, the respective third, fourth and fifth upper times corresponding to a respective third, fourth and fifth upper approximation of the upper boundary of the rest period;

determining the raw data lower intersection point where the motion data intersects with the threshold activity level based on the fifth upper time being used as a starting point for determining the raw data upper intersection point, wherein the raw data upper intersection point occurs within the motion data after the first upper time.

11. The system of claim 10, wherein determining the lower boundary of the rest period further comprises:

determining respective third, fourth, and fifth lower intersection points where the third, fourth and fifth data sets intersect with the threshold activity level based on a respective second, third and fourth lower time being used as a starting point for determining the respective third, fourth and fifth lower intersection points;

determining respective third, fourth, and fifth lower times within the given time interval associated with the respective third, fourth and fifth upper intersection points, the respective third, fourth and fifth lower times corresponding to a respective third, fourth and fifth approximation of the lower boundary of the rest period;

determining the raw data lower intersection point where the motion data intersects with the threshold activity level based on the fifth upper time being used as a starting point for determining the raw data upper intersection point, wherein the raw data lower intersection point occurs within the motion data after the first lower time.

12. The system of claim 9, wherein:
the first data filter comprises a first Gaussian window having a first length of 100 minutes;
the second data filter comprises a second Gaussian window having a second length of 80 minutes;
the third data filter comprises a third Gaussian window having a third length of 60 minutes;
the fourth data filter comprises a fourth Gaussian window having a fourth length of 40 minutes; and
the fifth data filter comprises a fifth Gaussian window having a fifth length of 20 minutes.

13. A wearable motion tracker, comprising:
at least one motion sensor that captures motion data representative of an amount of activity detected during each epoch of a given temporal duration experienced by the at least one motion sensor within a time period greater than the given temporal duration;
memory that stores the motion data; and
at least one processor configured to:
  set a threshold activity level for a rest period, wherein the threshold activity level is expressed in terms of an activity count during each epoch of the given temporal duration;
  apply at least a first data filter and a second data filter, different from the first data filter, to the motion data to generate at least a first data set and a second data set different from the first data set, representative of the motion data;
  determine a minimum point within the first data set;
  determine a minimum time within the given time interval associated with the minimum point;
  determine an upper boundary of the rest period, via the step of:
    determining a first upper intersection point where the first data set intersects with the threshold activity level, wherein the first upper intersection point occurs after the minimum time;
    determining a first upper time within the time period associated with the first upper intersection point, the first upper time corresponding to a first approximation of the upper boundary of the rest period;
    determining a second upper intersection point where the second data set intersects with the threshold activity level based on the first upper time being used as a starting point for determining the second upper intersection point;
    determining a second upper time within the period time associated with the second upper intersection point, the second upper time corresponding to a second approximation of the upper boundary of the rest period;
    determining a first position on the motion data corresponding to the second upper time;
    determining a raw data upper intersection point where the motion data intersects with the threshold activity level based on the second upper time being used as a starting point for determining the raw data upper intersection point, wherein the raw data upper intersection point occurs within the motion data after the first upper time;
    determining a raw data upper time within the time period associated with the raw data upper intersection point, wherein the raw data upper time occurs after the first upper time within the rest period; and
    assigning the raw data upper time as being the upper boundary of the rest period;
  determine a lower boundary of the rest period, via the steps of:
    determining a first lower intersection point where the first data set intersects with the threshold activity level, wherein the first lower intersection point occurs prior to the minimum time;
    determining a first lower time within the time period associated with the first lower intersection point, the first lower time corresponding to a first approximation of the lower boundary of the rest period;
    determining a second lower intersection point where the second data set intersects with the threshold activity level based on the first lower time being used as a starting point for determining the second lower intersection point;
    determining a second lower time within the time period associated with the second lower intersection point, the second lower time corresponding to a second approximation of the lower boundary of the rest period;
    determining a second position on the motion data corresponding to the second lower time;
    determining a raw data lower intersection point where the motion data intersects with the threshold activity level based on the second lower time being used as a starting point for determining the raw data lower intersection point, wherein the raw data lower intersection point occurs in the motion data prior to the first lower time;
    determining a raw data lower time within the time period associated with the raw data lower intersection point, wherein the raw data lower time occurs before the first lower time within the rest period; and
    assigning the raw data lower time as the lower boundary of the rest period; and
  determine an amount of time of the rest period, identified via the upper boundary of the rest period and the lower boundary of the rest period, by calculating a temporal difference between the raw data upper time and the raw data lower time.

* * * * *